United States Patent [19]

Scher

[11] 4,285,720
[45] Aug. 25, 1981

[54] ENCAPSULATION PROCESS AND CAPSULES PRODUCED THEREBY

[75] Inventor: Herbert B. Scher, Moraga, Calif.

[73] Assignee: Stauffer Chemical Company, Westport, Conn.

[21] Appl. No.: 922,473

[22] Filed: Jul. 7, 1978

Related U.S. Application Data

[63] Continuation of Ser. No. 323,171, Jan. 12, 1973, abandoned, which is a continuation-in-part of Ser. No. 234,793, Mar. 15, 1972, abandoned.

[51] Int. Cl.³ .................... A01N 25/28; A01N 43/00; B01J 13/02
[52] U.S. Cl. .......................... 71/88; 71/64 F; 71/100; 71/DIG. 1; 252/316; 264/4; 424/32; 424/206; 424/278; 424/DIG. 8
[58] Field of Search .............. 252/316; 264/4; 424/10, 424/32, 278, 286, 320, DIG. 8, 206; 71/100, 64 F, 88

[56] References Cited

U.S. PATENT DOCUMENTS

| | | |
|---|---|---|
| 1,112,755 | 10/1914 | Bergstrom ............................. 424/10 |
| 2,540,210 | 2/1951 | Nikitin ................................... 424/10 |
| 2,957,804 | 10/1960 | Shuyler ............................... 424/10 X |
| 3,576,760 | 4/1971 | Gould et al. ....................... 424/32 X |
| 3,577,515 | 5/1971 | Vandegaer ........................ 252/316 X |
| 3,701,759 | 10/1972 | Lee et al. .......................... 424/278 X |
| 3,726,804 | 4/1973 | Matsukawa et al. ................ 252/316 |

FOREIGN PATENT DOCUMENTS

| | | |
|---|---|---|
| 1415039 | 9/1965 | France ................................... 252/316 |
| 43740 | 11/1972 | Japan .................................... 252/316 |
| 1091076 | 11/1967 | United Kingdom ................... 252/316 |

Primary Examiner—Richard D. Lovering
Attorney, Agent, or Firm—Harry A. Pacini

[57] ABSTRACT

Encapsulation process to prepare encapsulated water-immiscible material employing an organic polyisocyanate intermediate to form a polyurea capsule enclosure around a water-immiscible material dispersed in an aqueous continuous phase comprising the steps of heating the dispersion or adding a catalyst, and optionally adjusting the pH to a value between 0 and 14.

106 Claims, 3 Drawing Figures

ENCAPSULATION PROCESS AND CAPSULES PRODUCED THEREBY

This application is a continuation of application Ser. No. 323,171 filed Jan. 12, 1973, now abandoned, which in turn is a continuation-in-part application of Ser. No. 234,793 filed Mar. 15, 1972, now abandoned.

BACKGROUND OF THE INVENTION

This invention relates to encapsulation and particularly to the production of small or minute capsules constituted by a skin or a thin wall of organic composition enclosing a body of material such as a liquid. The process of this invention is directed to the production of such capsules which may be produced to a predetermined size, and in a convenient and rapid method by chemical reaction in situ, wherein a suspension or a collection of discrete spheres or capsular spheroids is formed in a body of liquid which then may be readily separated or retained and used in said liquid.

Capsules of this nature and description have a variety of uses, such as for containing dyes, inks, chemical reagents, pharmaceuticals, flavoring materials, fungicides, bactericides, pesticides, such as herbicides, insecticides and the like, which substances can be dissolved, suspended or otherwise dispersed in or as the material to be enclosed by the capsule. The material to be encapsulated can be employed in the initial dispersion at a temperature above its melting point, or dissolved or dispersed in suitable water-immiscible organic solvent. The nature of the water-immiscible material to be encapsulated can be organic or inorganic in origin. Once encapsulated, the liquid or other form is preserved until it is released by some means or instrumentality that breaks, crushes, melts, dissolves or otherwise removes the capsule skin, or until release by diffusion is effected under suitable conditions. An important specific aspect of this invention, together with other features and advantages contemplated by the invention, is the procedure for polymerization involving the reaction between polyisocyanate monomers, to produce a capsular skin of polyurea.

DESCRIPTION OF THE PRIOR ART

A variety of techniques have been heretofore used or described for encapsulation purposes. Among these is the method, wherein the enclosing film is deposited by condensation and other procedures which involve polymerizing a substance contained in droplets or in a surrounding continuous liquid phase, so as to deposit the resulting polymer at the surface of such droplets. Another method involves the shooting of droplets through a falling film of liquid capsule-wall material which then solidifies around the individual droplets. Various methods of encapsulation by interfacial condensation between direct-acting, complimentary reactants are known. Within these methods are reactions for producing various types of polymers as the capsule walls. Many of such reactions to produce the coating substance occur between an amine which must be of at least difunctional character and a second reactant intermediate of acid or, more accurately, acid-derived nature, which for producing a polyamide is a difunctional or polyfunctional acid chloride. The amines chiefly used or proposed in these methods are typified by ethylene diamine or the like, having at least two primary amino groups.

For many processes of encapsulation, there is a final requirement of separation of the encapsulated materials from the forming media. During the handling process, the capsule wall material is subjected to great stresses and strains. For this reason, the highly desirable thin skin or cell wall is greatly restricted in the prior art methods. A particular object of the present invention is to provide a new and improved encapsulation process which is rapid and effective and which avoids the necessity of separation of the encapsulated material. A special advantage, therefore, is the permissible formation of extremely thin skin or cellular wall in conjunction with the capsules.

Interfacial polymerization generally involves bringing together two immiscible liquids, e.g., water and organic solvent, respectively, containing complimentary, direct-acting, organic intermediates that will react with each other to establish a solid polycondensate. Such polycondensates, such as a polyamide, polyester, polyurethane, polyurea, or like substances, can be formed from resin intermediates or monomers. It has also been proposed to spray droplets of organic solvent containing a diacid chloride into an aqueous liquid containing, for instance, ethylene glycol with the object of encapsulating the organic liquid or oil in polyester capsules. These efforts have fallen short of a practical value in various respects. For example, special apparatus is required for this technique. Further, various experiments have indicated the difficulty in establishing the desired capsules in discrete form whereby coalescense of the partially formed capsules into a heterogeneous mass of materials lacking distinct capsule formation will result. Control of capsule size or uniformity is troublesome in the prior art method. The processes appear limited in types of reactions and products involved. One particular method of encapsulation by interfacial polycondensation is disclosed in U.S. Pat. No. 3,577,515, issued May 4, 1971. This patent describes a continuous or batch method which requires a first reactant and a second reactant complimentary to the first reactant with each reactant in separate phases, such that the first and second reactant react at the interface between the droplets to form encapsulated droplets. As will become apparent hereinafter, the instant invention eliminates the necessity for a second reactant wherein it has been found that a polyurea type encapsulation body can be formed with great ease and provides special advantages.

SUMMARY OF THE INVENTION

In contradistinction to the prior art and in accordance with the preferred practice of the present invention, it has been discovered that effective encapsulation by interfacial polymerization of an organic isocyanate intermediate can be effected in a process which utilizes two substantially immiscible liquids, one termed an aqueous phase and the other termed an organic phase, and which comprises establishing a physical dispersion of the organic phase in the aqueous phase, said organic phase containing the organic isocyanate intermediate for the polyurea capsule skin or enclosure. The interfacial polymerization of the present invention to form the capsular wall involves hydrolysis of an isocyanate monomer to form an amine which in turn reacts with another isocyanate monomer to form the polyurea enclosure. During the hydrolysis of the isocyanate monomer, carbon dioxide is liberated. The addition of no other reactant is required once the dispersion establishing droplets of the organic phase within a continuous liquid phase, i.e., aqueous phase, has been accomplished. Thereafter, and preferably with moderate agitation of the dispersion, the formation of the polyurea capsule skin or enclosure around the dispersed organic droplets is brought about by heating the continuous liquid phase or by introducing a catalytic amount of a basic amine or other agent capable of increasing the rate of isocyanate hydrolysis, such as tri-n-butyl tin acetate, optionally in addition adjusting the pH of the dispersion, thereby effecting the desired condensation reaction at the interface between the organic droplets and the continuous phase.

In this fashion, fully satisfactory, discrete capsules are formed having a skin consisting of the polyurea produced by the reaction and containing the encapsulated material. Within the process of the invention the reaction which forms the skin or enclosure for the capsule generally is complete, such that essentially no unreacted polyisocyanate remains. It is not necessary to separate the capsules for desired utilization, i.e., the encapsulated material may be directly usable, depending upon the intended utilization. However, such separation prior to utilization may be carried out by any of the normal separation processes involving, for example, settling, filtration or skimming of the collected capsules, washing and, if desired, drying. The product from the process of this invention is particularly suitable for direct agricultural pesticidal applications, additional agents can be added such as thickeners, biocides, surfactants and dispersants to improve storage stability and ease of application. The initial dispersion of the organic phase in the aqueous phase may be assisted with an appropriate emulsifying or dispersing agent and the control of the size and uniformity of the ultimate capsules is readily effected by any convenient method to disperse one liquid into another.

DETAILED DESCRIPTION OF THE INVENTION

In all cases, within the practice of the present invention, the effective procedure involves first, producing, as by simple agitation, a solution of water, a suitable surfactant and protective colloid. These three ingredients comprise the aqueous phase or continuous phase of the process. The aqueous or continuous phase is essentially free of any components that will react with the material therein or any of such group of materials. The surfactant and protective colloid in the aqueous phase do not enter into the polycondensation reaction by which the capsule wall is formed.

By way of further exemplification, the surfactants in the aqueous or continuous phase can be described as nonionic, anionic, or cationic surfactants in the HLB (hydrophile-lipophile balance) range from about 12 to about 16. There are many surfactants which satisfy this HLB range requirement. Among the acceptable surfactants are the compounds known as sodium isopropyl naphthalene sulfonate, polyoxyethylenesorbitol oleate laurate, ethoxylated nonylphenols, however, the preferred surfactant is of the class polyethylene glycol ethers of linear alcohols. Whereas the surfactant is described herein as placed in the aqueous phase, it can also be placed in the organic phase. Without specific reference to the phase in which the surfactant is placed, there will be a partitioning and distribution of the surfactant between each phase upon the mixing of the phases depending upon the relative solubility therein. Use of a surfactant may be omitted provided that a sufficiently high shear rate is employed to form the dispersion. In the preferred embodiment of this invention a surfactant is employed. The range of surfactant concentration found most acceptable in this system is from about 0.01 percent to about 3.0 percent by weight based on the aqueous phase. Higher concentrations of surfactant may be used without increased ease of dispersibility.

Also present in the aqueous or continuous phase is a protective colloid which can be selected from a wide range of such materials. The usable protective colloids can be exemplified by the following: Polyacrylates, methyl cellulose, polyvinyl alcohol, polyacrylamide and poly(methylvinyl ether/maleic anhydride). The amount of colloid employed will depend upon various factors such as molecular weight, type and effectiveness within the media, compatability and the like. It has been found that the protective colloid can be added to the aqueous phase prior to addition of the organic phase to the aqueous phase. Alternatively, the protective colloid can be added to the system following the addition of the organic phase or following the dispersion thereof. As another alternative, the protective colloid can be added partially prior to addition of the organic phase and partially after the dispersion step. Generally, from about 0.1 percent to about 5.0 percent by weight based on the aqueous phase is used.

A second phase, known as the organic phase, comprises the material to be encapsulated, and a polyisocyanate. The material to be encapsulated can be used in a concentrated form or in a solution of a water-immiscible solvent. The material to be encapsulated can be used as the solvent for the polyisocyanate. However, to achieve a desired concentration of active material in the final product, a water-immiscible organic solvent can be used to dissolve the material to be encapsulated and polyisocyanate. The material to be encapsulated and the polyisocyanate are added simultaneously to the aqueous phase. Whereas, the material to be encapsulated and the polyisocyanate may be added separately with slow agitation in the reactor for a time sufficient to cause a homogeneous organic solution, the preferred method of simultaneous addition of the components of the organic phase is in a pre-mixed state. That is, the material to be encapsulated and the polyisocyanate are pre-mixed to obtain a homogeneous phase before addition to and mixing with the aqueous phase. The amount of the organic phase may vary from about 1 percent to about 75 percent by volume of the aqueous phase present in the reaction vessel. The concentrations in the lower end of the range are relatively undesirable since they result in a very dilute suspension of capsules. The preferred amount of organic phase is about 25 percent to about 50 percent by volume.

The nature of the organic polyisocyanate determines the release properties of the capsule formed by this process. The polyisocynates also determine the structural physical strength of the capsular skin. The organic polyisocyanates contemplated in this process include those members of the aromatic polyisocyanate class which includes the aromatic diisocyanates, the aliphatic diisocyanate class, high molecular weight linear aliphatic diisocyanates and the isocyanate pre-polymers. Representative of the aromatic diisocyanates and other polyisocyanates are the following:

1-Chloro-2,4-phenylene diisocyanate
m-Phenylene diisocyanate
p-Phenylene diisocyanate
4,4'-Methylenebis (phenyl isocyanate)
2,4-Tolylene diisocyanate
Tolylene diisocyanate (60% 2,4-isomer, 40% 2,6-isomer)
2,6-Tolylene diisocyanate
3,3'-Dimethyl-4,4'-biphenylene diisocyanate
4,4'-Methylenebis (2-methylphenyl isocyanate)
3,3'-Dimethoxy-4,4'-biphenylene diisocyanate
2,2',5,5'-Tetramethyl-4,4'-biphenylene diisocyanate
80% 2,4- and 20% 2,6-isomer of tolylene diisocyanate
Polymethylene polyphenylisocyanate (PAPI)

It is highly desirable to use combinations of the above-mentioned organic polyisocyanates. Such combinations as, for example, polymethylene polyphenylisocyanate and tolylene diisocyanate, containing 80% 2,4- and 20% 2,6-isomers, produce excellent capsular enclosures with exceptional controlled release properties.

The amount of organic polyisocyanate used in the process will determine the wall content of the capsules formed therein. Generally, based on the organic phase, there will be greater than about 2 percent by weight organic polyisocyanate present. However, this is by no means limiting and a greater amount can be used that is approaching 100 percent. Clearly, 100 percent would not be entirely desirable since this would result in a product with no encapsulated material. The preferred range is from about 2.0 percent to about 75.0 percent by weight of organic polyisocyanate, thereby forming an encapsulated product having a corresponding wall content, i.e., about 2.0 percent to about 75.0 percent. More particularly, the preferred range is from about 5.0 percent to about 50.0 percent wall content.

Figure 1:
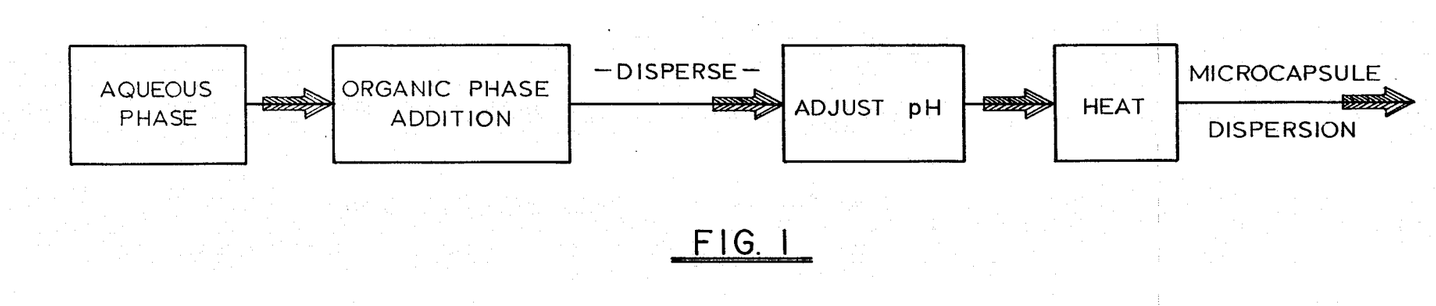
FIG. 1 is a schematic representation of one embodiment of a process according to the instant invention for preparing capsule dispersions.

In accordance with preferred practice of the present invention, the following general steps comprise the process which utilizes the two substantially immiscible phases described above. In essence, the process comprises establishing a physical dispersion of the organic phase in the aqueous or continuous phase, such dispersion thereby establishing droplets of desired size in the aqueous phase. Thereafter, by adjusting the pH of the resulting mixture, and temperature within the appropriate temperature range, the desired condensation reaction is thereby effected at the interfaces between the droplets and the continuous phae, FIG. 1. Certain variations in the sequence of steps between adjustment of the pH and addition of required heat will be apparent in the following discussion and examples.

Figure 3:
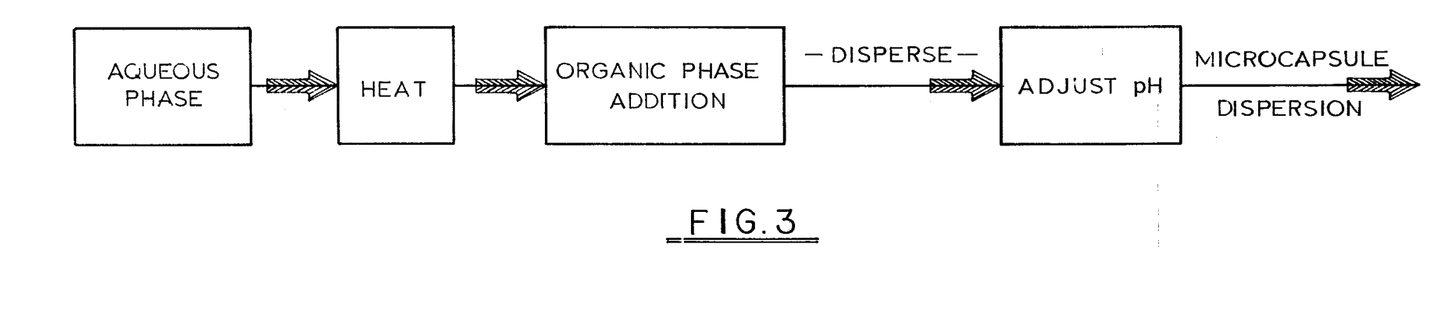
FIG. 3 is a schematic representation of a third embodiment of a process according to the instant invention for preparing capsule dispersions.

The temperature of the two-phase mixture, that is, the dispersion of the organic phase in the aqueous phase, is raised to about 40° C. to about 60° C. The temperature range for the condensation reaction within the present invention is between about 20° C. to about 90° C. Whereas the heat to initiate the reaction can be applied to the dispersion of the organic phase in the aqueous phase simultaneously or after the adjustment of the pH to the desired value, the aqueous phase can be heated to the required temperature prior to the steps of addition of the organic phase and dispersion, FIG. 3. In this alternative procedure, the adjustment of the pH is performed after the dispersion is accomplished and the pH is maintained within the limits to be discussed below.

Figure 2:
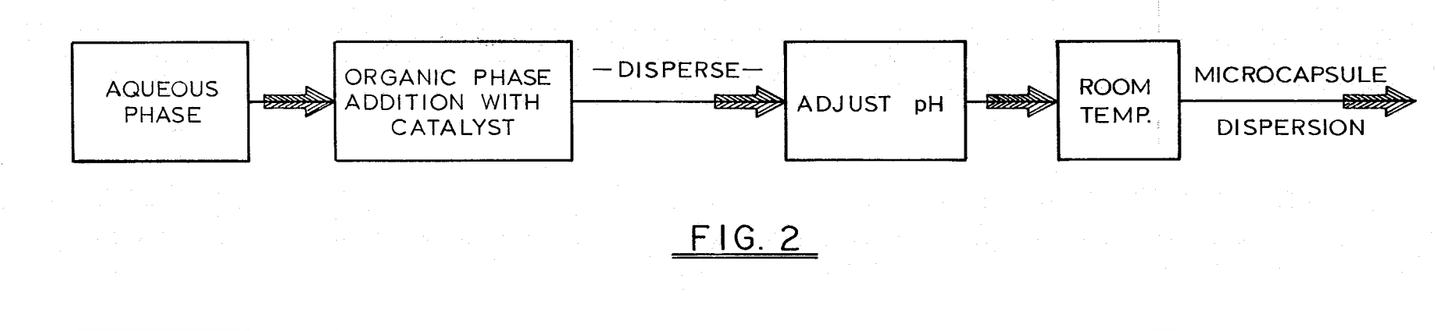
FIG. 2 is a schematic representation of a second embodiment of a process according to the instant invention for preparing capsule dispersions.

Within one embodiment of the present invention, FIG. 2, it has been found that a catalyst capable of increasing the rate of isocyanate hydrolysis, for example, the basic amine type, may be added to the organic phase or aqueous phase prior to the initiation of the desired condensation reaction. However, this step is not necessary to the successful practice of the present invention. When it is selected to substitute a catalyst for the increase in temperature in the process, the product obtained thereby is comparable to a non-catalyzed system. Increased temperature and catalyst can be used simultaneously to effect the desired polycondensation reaction. The catalyst in such a procedure is added preferably to the organic phase and is added to the system at the time of mixing of the aqueous and organic phases. Various catalysts have been found acceptable, their selection will depend upon factors easily determinable by one skilled in the art. It has been found that certain basic organic amines, preferably the tertiary amines, and alkyl tin acetates such as tri-butyl tin acetate and di-n-butyl tin diacetate are acceptable catalysts. When an alkyl tin acetate is used, about 0.001 percent to about 1.0 percent by weight based on the organic phase is employed. Included among the basic organic tertiary amines are triethylene diamine, N,N,N',N'-tetramethyl-1,3-butane-diamine, triethylamine, tri-n-butyl amine and the like. The amount of catalyst will vary with the particular system and conditions. When a basic organic amine is used, about 0.1 percent to about 10.0 percent by weight based on the organic phase is employed.

Oftentimes it will be found that water will be slightly soluble in the water-immiscible material to be encapsulated. The amount of water which will be dissolved in the material to be encapsulated will depend upon the nature of the material. Usually the amount of water dissolved will be relatively minor. However, when using a water-immiscible material that can dissolve an appreciable quantity of water, slight deviation in the normal processes described herein is preferred. In such a system it has been found that particles with poorly defined wall structure result. Well-defined microcapsules within the description of this invention can be prepared by adding an appropriate catalyst to the aqueous phase after the emulsion is formed. Thereby, the bulk of the polymerization takes place at the interface where the catalyst is present. No heating of the process mixture is advised, otherwise polymer will form not only on the surface, but an increased proportion will form within the water-immiscible material that can dissolve an appreciable amount of water. This procedure is preferably performed at about room temperature (15° to 30° C.). This method of addition of the catalyst to the aqueous phase after dispersion is not limited to encapsulation of only water-immiscible material that can dissolve appreciable quantity of water, but finds general applicability with any water-immiscible material herein discussed and described.

It is satisfactory to prepare the aqueous phase as described above. While stirring the aqueous phase, the organic phase is added, preferably in a pre-mixed state. Upon addition of the organic phase to the aqueous phase, a suitable dispersing means to disperse one liquid into the other is employed. Any high shear device can be used conveniently to obtain the desired droplet size within the range of from about 0.5 microns to about 4,000 microns. The actual range will depend upon the desired end use. As an example, the preferred range for most pesticidal applications is from about 1 micron to about 100 microns. This instant process is applicable to preparing widely varied but uniform sized capsules. Once the proper droplet size is obtained, the dispersion means employed to establish the desired droplet size is discontinued. Only mild agitation is required for the balance of the process.

The process of the instant invention is capable of satisfactory performance and production of encapsulated material without adjustment to a specific pH value. That is, no adjustment of the pH of the system need be made during the encapsulation process. The encapsulation process will proceed at a pH value of between about 0 to about 14. The desirability of any adjustment of pH to a particular value will depend upon the nature of the systems components, such as surfactant, colloid, catalyst, temperature, material to be encapsulated and the like. For example, if the pH is allowed to drop below about 7.0, carbon dioxide will be liberated during the course of the reaction. If it is desirable to eliminate this evolution of carbon dioxide, then adjustment can be made to a pH value at least about 7.0. Within the embodiment, FIG. 1 and FIG. 2, the pH is adjusted after dispersion and maintained at that value for the remainder of the condensation reaction. The adjustment of the pH can take place in the aqueous phase prior to the addition and dispersion therein of the organic phase. The adjustment and maintenance of a particular pH throughout the reaction can be accomplished with various water soluble bases or acids nonreactive with the polyisocyanate intermediate. Preferably, concentrated sodium hydroxide (25% solution), potassium hydroxide, hydrochloric acid and the like can be used.

The evolution of carbon dioxide may cause considerable undesirable foam formation and/or volume expansion which interferes with the processing of the reaction mixture. An alternative to the adjustment of the pH in order to eliminate the excessive foam produced by the carbon dioxide evolution is the addition of a defoamer. By the use of a defoamer, it is possible to satisfactorily produce the encapsulated material at an acid pH without the addition of caustic to the acidic system. The defoamer can be added at any time to the processing mixture wherein said polymer capsular enclosures are formed to encapsulate a water-immiscible material.

Whereas the desired condensation reaction at the interface between the droplets and the continuous phase occurs very rapidly, the majority within the first one-half hour of reaction time, in order to insure near completion of the condensation reaction throughout the system, the reaction conditions are continued for from about 2 to 3 hours. Under properly adjusted conditions or with a proper catalyst, the reaction time can be shortened. At the end of this time, the formation of a capsule wall has been completed, thereby encapsulating the organic material within the skin of a polycondensate, and there exists a usable encapsulated product. A specific feature of the present invention, which is highly desirable, resides in the fact that for certain intended applications, no further separation or handling of the encapsulated material is required, i.e., the product is directly usable. The encapsulated material can be used for various direct applications at this point or indirectly by incorporating the material into other products. The thickness or chemical composition of the capsule-wall can be selected or controlled in various ways. For example, these properties can be affected by control of the reaction condition, by chemical selection, especially in the creation of cross-linkage which is determined by the functionality of the polyisocyanate in accordance with the invention. The thickness of the capsule skin can also be altered by varying the amounts of reactants within the organic phase. One convenient mode of controlling the size of the capsule is adjustment of the speed of agitation, that is, in bringing about the original dispersion of the organic phase, smaller capsules can be obtained with higher speeds of agitation resulting in a greater shearing force.

Tests have indicated that capsules produced in accordance with the present invention can be utilized in the same manner as products of other encapsulation procedures. Thus, for example, encapsulated herbicides or insecticides can be embodied in dispersions for application purposes, for controlled release of the encapsulated material at the desired locality. Special utility is noted for the encapsulation of various volatile or unstable insecticides and herbicides. By encapsulation, premature volatilization or other deterioration of the material is avoided; such encapsulation can also serve the purpose of retarding or delaying action to the time when desired. Controlled release of these materials is important for environmental protection and the proper effect on the organism to be controlled, as well as decreased toxicity on beneficial organisms.

The present invention may be practiced in a batch or batch-like form or in a continuous or continuous-like form. When the invention is practiced in a manner resembling a batch process, all the various liquids and various reactants will be brought together and various steps determined by the proper time sequence into a single body of liquid. The batch process may be altered by using the suitable reactors such that a continuous or continuous-like form of the encapsulation process is achieved. In the continuous form of the inventive process, dispersion and agitation of the reacting phases may continuously be practiced at a proper rate to continuously form a suitable dispersion of droplets in the continuous phase and such that a continuously supplied portion of the dispersion of droplets in a continuous phase is added to a reactor in which the pH can be adjusted and the appropriate heat applied to achieve the condensation. Within the continuous system, the proper rate for reaction may be obtained by selecting the appropriate conditions. Both the batch and continuous aspects of the present invention are highly desirable, and choice there between will rest solely with the desired manufacturing conditions.

EXAMPLE I

Water (500 cc.), containing 1.0% of neutralized poly-(methyl vinyl ether/maleic anhydride) protective colloid (Gantrez AN 139) and 0.2% linear alcohol ethoxylate emulsifier (Tergitol 15-S-20) is placed into an open reactor vessel. In a separate container 167 g. O-ethyl S-phenyl ethylphosphonodithioate (an insecticide), 39 g. polymethylene polyphenylisocyanate (PAPI) and 19.5 g. tolylene diisocyanate (TDI 80% 2,4 and 20% 2,6) are mixed together. This mixture is then added to the reactor vessel and emulsified with a high shear stirrer. The resulting particle size range is about 1 to about $20\mu$. Only mild agitation is required for the balance of the reaction. The temperature of the reactants is raised to 50° C. over a 17 minute period and at the same time, the pH of the dispersion is maintained at 8.5 by addition of 25% sodium hydroxide solution. The temperature of the reaction mixture is maintained at 50° C. and the pH is maintained at 8.5 for 2½ hours in order to complete the interfacial polymerization.

At this point, 0.25% sodium bentonite thickener and 0.05% sodium pentachlorophenate biocide for example, can be added to formulate the product without separation or further washing. The pH of the formulation is usually adjusted to 9.75 by addition of 25% NaOH solution and the reaction mixture cooled to room temperature. These formulations disperse very well in water and discrete capsules are observed under a microscope. These capsules have a wall content of about 26 percent.

EXAMPLE II

Water (500 cc.), containing 1.5% hydroxypropylmethyl cellulose protective colloid (Methocel 65HG) and 0.2% linear alcohol ethoxylate emulsifier (Tergitol 15-S-20) is placed into an open reactor vessel. In a separate container, 150 g. S-ethyl diisobutylthiocarbamate (an herbicide), 35 g. polymethylene polyphenylisocyanate (PAPI), 17.5 g. tolylene diisocyanate (TDI 80% 2,4 and 20% 2,6) and 0.05 g. of tributyl tin acetate catalyst are mixed together. This mixture is then added to the reactor vessel and emulsified with a high speed stirrer. The resulting particle size range is about 1 to about 20μ. Only mild agitation is required for the balance of the reaction. The pH of the reaction mixture is now adjusted to 8.0 with 10% sodium hydroxide solution. This pH is maintained for 3 hours by continued addition of 10% sodium hydroxide solution. The presence of the catalyst allows the interfacial polymerization to be conducted at room temperature (25° C.). The formulation disperses very well in water and discrete capsules can be observed under a microscope. These capsules have a wall content of about 26 percent.

EXAMPLE III

Water (500 cc.), containing 0.5% polyacrylamide protective colloid (Cyanamer A370) and 0.2% linear alcohol ethoxyate (Tergitol 15-S-20) is placed into an open reactor vessel. In a separate container, 167 g. O-ethyl S-phenyl ethylphosphonodithioate (an insecticide), 14.5 g. polymethylene polyphenylisocyanate (PAPI) and 14.5 g. tolylene diisocyanate (TDI 80% 2,4 and 20% 2,6) are mixed together. The aqueous phase in the open reactor vessel is heated to 45° C. after which the above organic mixture is added to the reactor and emulsified with a high shear stirrer. At this point, the pH is equal to about 6.5. The resulting particle size range is 1–20μ. Only mild agitation is required for the balance of the reaction. The pH of the reaction mixture is adjusted to 8.5 with 25% sodium hydroxide solution. The temperature of the reaction mixture is adjusted to 50° C. The temperature and pH of the reaction mixture are maintained at 50° C. and 8.5, respectively, for 3 hours in order to complete the interfacial polymerization. The pH is maintained at 8.5 by continued addition of 25% sodium hydroxide solution. At this point 0.25% sodium bentonite thickener can be added to the capsule dispersion and the pH adjusted to 9.8 to formulate the encapsulated material without further separation or handling. The formulation is cooled to room temperature. This formulation can be dispersed readily in water and discrete capsules can be observed under a microscope. These capsules have a wall content of about 15 percent.

EXAMPLE IV

Water (100 cc.), containing 3% of polyacrylate protective colloid (Goodrite K-718) and 0.2% linear alcohol ethoxylate emulsifier (Tergitol 15-S-20) is placed into an open reactor vessel. In a separate container, 30 g. of 4'-ethylphenyl geranyl ether-6,7-epoxide (insect hormone mimic) and 2.4 g. of tolylene diisocyanate (TDI 80% 2,4- and 20% 2,6-) are mixed together. This mixture is then added to the open reactor vessel and emulsified with a high shear stirrer. The resulting particle size range is 1–20μ. Only mild agitation is required for the balance of the reaction. In order to increase the rate of interfacial polymerization, the temperature of the reactants is now raised to 50° C. over a 15 minute period and at the same time, the pH of the dispersion is maintained at 8.5 by addition of 10% sodium hydroxide solution. The temperature and pH of the reaction mixture is maintained at 50° C. and 8.5, respectively, for 2 hours in order to complete the interfacial polymerization. The pH of the formulation is adjusted to 8.9. The formulation was cooled to room temperature. This formulation disperses very well in water and discrete capsules can be observed under a microscope. These capsules have a wall content of about 7.4 percent.

EXAMPLE V

Water (500 cc.), containing 1.0% polyvinyl alcohol protective colloid (Vinol 540) and 0.2% linear alcohol ethoxylate emulsifier (Tergitol 15-S-20) is placed into an open reactor vessel. The temperature of this solution is raised to 40° C. In a separate container, 30 g. of S-ethyl dipropylthiocarbamate (an herbicide) and 10 g. of polymethylene polyphenylisocyanate (PAPI) are mixed together. This mixture is then added to the reactor vessel and emulsified with a high speed stirrer. The temperature of the system is then raised to 60° C. and mild agitation is continued for 1½ hours while the temperature is maintained at 50° C. The material is then filtered and washed three times and then allowed to dry at room temperature. Microscopic observation shows discrete spheroid particles. The capsules have a wall content of 25 percent.

EXAMPLE VI

Water (500 cc.) containing 3.0% hydroxypropylmethyl cellulose protective colloid (Methocel 65 HG) and 0.2% linear alcohol ethoxylate emulsifier (Tergitol 15-S-20) is placed into an open reactor vessel. In a separate container, 150 g. S-ethyl dipropylthiocarbamate (an herbicide), 35 g. polymethylene polyphenylisocyanate (PAPI), 17.5 g. tolylene diisocyanate (TDI 80% 2,4- and 20% 2,6-) and 0.05 g. tributyl tin acetate catalyst are mixed together. This mixture is then added to the reactor vessel and emulsified using a high speed stirrer. The resulting particle size is about 5 microns. Only mild agitation is required for the balance of the reaction. The temperature of the system is slowly raised to 50° C. over a 1½ hour period. At 50° C., considerable foaming took place. The system is kept at 50° C. for an additional 1½ hour after which it is cooled to room temperature. Microscopic examination of the system showed discrete, well-formed capsules. These capsules have a wall content of 26 percent.

EXAMPLE VII

Water (500 cc.), containing 3% polyacrylate protective colloid (Goodrite K-718) and 0.3% linear alcohol ethoxylate emulsifier (Tergitol 15-S-7) is placed into an open reactor vessel. In a separate container, 30 g. of S-ethyl diisobutylthiocarbamate (an herbicide), 6.7 g. polymethylene polyphenylisocyanate (PAPI) and 3.3 g. tolylene diisocyanate (TDI 80% 2,4 and 20% 2,6) are mixed together. The organic phase then is added to the reactor and emulsified with a high shear stirrer. The resulting particle size range is about 1–10μ. Only mild agitation is required for the balance of the reaction. The pH of the reaction mixture is adjusted to 4.5 with concentrated hydrochloric acid. The temperature of the reaction mixture is raised to 50° C. and maintained at that temperature for 3 hours. The system is cooled to room temperature. The pH remained at 4.5 during the course of the reaction. This product can be dispersed readily in water and discrete capsules can be observed under the microscope. These capsules have a wall content of about 25 percent.

EXAMPLE VIII

Water (900 cc.), containing 0.3% linear alcohol ethoxylate emulsifier (Tergitol 15-S-7) is placed into an open reactor vessel. In a separate container, 334 g. of S-ethyl diisobutylthiocarbamate (an herbicide), 20.7 g. polymethylene polyphenylisocyanate and 20.7 g. tolylene diisocyanate (TDI 80% 2,4 and 20% 2,6) are mixed together. The organic phase is then added to the reactor and emulsified with a high shear stirrer. The resulting particle size range is 5–15μ. Only mild agitation is required for the balance of the reaction. One hundred grams of 5.0% aqueous solution of polyacrylamide protective colloid (Cyanamer A-370) is then added to the reaction mixture. The temperature of the reaction mixture is raised to 50° C. and at the same time, the pH of the dispersion is maintained at 8.5 by addition of 25% sodium hydroxide solution. The temperature of the reaction mixture is maintained at 50° C. and the pH is maintained at 8.5 for about 3 hours in order to complete the interfacial polymerization. The reaction mixture is cooled to room temperature. The reaction mixture can be dispersed readily in water and discrete capsules can be observed under the microscope. These capsules have a wall content of about 11 percent.

EXAMPLE IX

This example illustrates the use of a highly basic pH value (i.e. pH=13.6).

Water (500 cc.), containing 2.0% hydroxypropylmethyl cellulose protective colloid (Methocel 65 HG), 0.2% linear alcohol ethoxylate emulsifier (Tergitol 15-S-20) and 1.5% sodium hydroxide (pH=13.6) is placed into an open reactor vessel. In a separate container, 150 g. S-ethyl diisobutyl thiocarbamate (an herbicide), 35.0 g. polymethylene polyphenylisocyanate (PAPI), 17.5 g. tolylene diisocyanate (TDI 80% 2,4 and 20% 2,6) and 0.05 g. tributyl tin acetate are mixed together. The aqueous phase is cooled down to 9° C. The organic phase is then added to the reactor vessel and emulsified with a high shear stirrer. All particles were reduced below 40μ in size. Only mild agitation is required for the balance of the reaction. The temperature was allowed to rise slowly to room temperature (22° C.). Stirring continued for approximately 16 hours. Discrete capsules were observed under a microscope. The capsules have a wall content of about 25 percent.

EXAMPLE X

This example illustrates the use of a highly acidic pH value (i.e. pH=0).

Water (500 cc.), containing 3.0% polyvinyl alcohol protective colloid (Vinol 540), 0.3% linear alcohol ethoxylate emulsifier (Tergitol 15-S-7) and 3.7% hydrochloric acid (pH=0) is placed into an open reactor vessel. In a separate container 150 g. S-n-propyl di-n-propyl thiocarbamate (an herbicide), 17.7 g. polymethylene polyphenylisocyanate (PAPI) and 8.8 g. tolylene diisocyanate (TDI 80% 2,4 and 20% 2,6) are mixed together. This mixture is then added to the reactor vessel and emulsified with a high shear stirrer. All particles were reduced below 15μ in size. Only mild agitation is required for the balance of the reaction. The temperature of the reactants is raised to 50° C. over a 20 minute period. The temperature of the reaction mixture is maintained at 50° C. for 2½ hours to complete the interfacial polymerization. Discrete capsules are observed under a microscope. The capsules have a wall content of about 15 percent.

EXAMPLE XI

This is an example of encapsulation of water-immiscible material which can dissolve an appreciable quantity of water, in this instance 5.4%.

Water (500 cc.), containing 1.0% polyacrylamide protective colloid (Cyanamer A370) and 0.3% linear alcohol ethoxylate (Tergitol 15-S-20) is placed into an open reactor vessel. In a separate container 33.4 g. tris-β-chloroethylphosphate (a flame retardant), 4.0 g. polymethylene polyphenyl isocyanate (PAPI) and 2.0 g. tolylene diisocyanate (TDI 80% 2,4 and 20% 2,6) are mixed together. The mixture is then added to the reactor vessel and emulsified with a high shear stirrer. The resulting particle size range is 2–15μ. Only mild agitation is required for the balance of the reaction. At this point, 1.0 g. triethylene diamine catalyst dissolved in 10 ml. water is added to the aqueous phase and the pH is adjusted to 9.5. The pH is maintained at 9.5 by addition of 25% sodium hydroxide solution and stirring continued at room temperature (about 25° C.) for 17 hours. Discrete, well-formed microcapsules are observed under a microscope. The capsules have a wall content of 15 percent.

EXAMPLE XII

This example illustrates the encapsulation of a normally solid material by enclosure formation around a water-immiscible solvent in which the solid material is dissolved.

Water (500 cc.), containing 2.0% of hydrolyzed poly(methyl vinyl ether/maleic anhydride) protective colloid (Gantrez AN119) and 0.3% linear alcohol ethoxylate emulsifier (Tergitol 15-S-7) is placed into an open reactor vessel. The pH of this solution is adjusted to 4.5. In a separate container, 167 g. of a 30% solution of N-(mercaptomethyl) phthalimide S-(O,O-dimethyl phosphorodithioate) (an insecticide with melting point of 72° C.) in heavy aromatic naphtha solvent (Panasol AN-3), 8.3 g. polymethylene polyphenyl isocyanate (PAPI) and 4.2 g. tolylene diisocyanate (TDI 80% 2,4 and 20% 2,6) are mixed together. This mixture is then added to the reactor vessel and emulsified with a high shear stirrer. All particles are reduced below 20μ in size. Only mild agitation is required for the balance of the reaction. This temperature of the reactants is raised to 50° C. over a 20 minute period. The temperature of the reaction mixture is maintained at 50° C. for 2½ hours to complete the interfacial polymerization. The formulation disperses very well in water and discrete capsules are observed under a microscope. The capsules have a wall content of about 7.5 percent. No crystals of insecticide are observed under a microscope after the preparation is stored at room temperature for 2 days.

EXAMPLE XIII

This example illustrates the encapsulation of two water-immiscible substances in the organic phase.

Water (500 cc.), containing 0.5% polyacrylamide protective colloid (Cyanamer A370) and 0.3% linear alcohol ethoxylate (Tergitol 15-S-7) is placed into an open reactor vessel and the pH adjusted to 8.5. In separate container, 138.5 g. S-ethyl dipropyl thiocarbamate (an herbicide), 11.5 g. N,N-dialkyldichloroacetamide (an herbicide antidote), 35.0 g. polymethylene polyphenyl isocyanate (PAPI) and 17.5 g. tolylene diisocyanate (TDI 80% 2,4 and 20% 2,6) are mixed together. This mixture is then added to the open reactor vessel and emulsified with a high shear stirrer. The resulting particle size range is 5–30μ. Only mild agitation is required for the balance of the reaction. The reaction mixture is then heated to 50° C. over a 26 minute period. The reaction mixture is maintained at 50° C. for 2½ hours. The pH is maintained at 8.5 by the addition of 25% sodium hydroxide solution. This formulation disperses very well in water and discrete microcapsules can be observed under a microscope. These capsules have a wall content of about 25 percent.

As previously mentioned and illustrated by the examples herein, the process for encapsulation of the instant invention provides capsules capable of controlling release of encapsulated organic material. Representative and especially of importance are the process and capsules comprising as a constituent in the organic phase herbicides of the class thiocarbamate such as S-ethyl diisobutylthiocarbamate; S-ethyl dipropylthiocarbamate; S-ethyl hexahydro-1-H-azepine-1-carbothioate; S-propyl hexahydro-1-H-carbothioate; S-propyl dipropylthiocarbamate; S-ethyl ethyl-cyclohexyl thiocarbamate; S-propyl butylethyl thiocarbamate; organo phosphorus insecticides of the class organo phosphono and phosphorothioates and dithioates such as O-ethyl S-phenyl ethyl-phosphonodithioate, S-[(p-chlorophenylthio)methyl] O,O-dimethyl phosphorodithioate, S-[(p-chlorophenylthio)methyl] O,O-diethylphosphorodithioate, O,O-dimethyl O-p-nitrophenyl phosphorothioate, O,O-diethyl O-p-nitrophenyl phosphorothioate; and insect hormones and mimics such as:

Cecropia—Juvenile Hormone—I

1-(4'-ethyl)phenoxy-3,7-dimethyl-6,7-epoxy-trans-2-octene

1-(3',4'-methylenedioxy)phenoxy-3,7-dimethyl-6,7-epoxy-trans-2-nonene

Ethyl 3,7,11-trimethyldodeca-2,4-dienoate

Isopropyl 11-methoxy-3,7,11-trimethyl-dodeca-2,4-dienoate

Capsules of compounds useful for plant disease control provide a route to long term control of disease using compounds generally regarded to have only short term effectiveness. Similarly, herbicides, nematocides, insecticides, rodenticides and soil nutrients can be encapsulated with useful results. Chemicals used for seed treatment are also readily encapsulated by the process of the invention. Other biological products can be encapsulated including: Anthelmintics, lamphrey and slime control agents, algicides, swimming pool chemicals, miticides, acaracides, animal attractants, antiseptics, deodorants, disinfectants, mildewicides, and the like.

The material to be encapsulated utilizing the process of the instant invention can be of any type which is water-immiscible. The material need not consist of only one type, but may be a combination of two or more various types of water-immiscible materials. For example, employing an appropriate water-immiscible material, such a combination is an active herbicide and an active insecticide. Also contemplated is a water-immiscible material to be encapsulated which comprises an active ingredient, such as an herbicide and an inactive ingredient such as a solvent or adjuvant. Encapsulation of a solid material can be accomplished by this method by forming a solution of the solid material in an appropriate solvent; thereby, normally solid water-immiscible material can be encapsulated. For example, the insecticide N-(mercaptomethyl) phthalimide S-(O,O-dimethyl phosphorodithioate), m.p. 72° C., can be encapsulated by first dissolving the solid in an appropriate solvent, such as heavy aromatic naphtha solvent.

What is claimed:
1. A process of encapsulating water-immiscible material within discrete capsules of polyurea without addi- tion of a second reactant, whereby hydrolysis of an isocyanate monomer to form an amine takes place which in turn reacts with another isocyanate monomer to form polyurea, which comprises the steps:

(a) providing, at room temperature, a dispersion of (i) a water-immiscible phase comprising the water-immiscible material to be encapsulated and an organic polyisocyanate in (ii) an aqueous phase comprising a solution of water, a surfactant and a protective colloid; and (b) heating and maintaining said dispersion in a temperature range of about 40° C. to about 90° C.; whereupon said water-immiscible material is encapsulated within discrete polyurea capsular enclosures directly usable without further separation or purification.

2. The process of claim 1 wherein the dispersed water-immiscible phase comprises droplets having a particle size of between about 0.5 microns to about 4000 microns.

3. The process of claim 2 wherein said dispersion is maintained by mild agitation.

4. The process of claim 3, wherein said water-immiscible phase contains a catalyst selected from the group consisting of (a) a basic organic tertiary amine catalyst in the amount of about 0.01 percent to about 10.0 percent by weight based on the organic phase and (b) an alkyl tin acetate catalyst in the amount of about 0.001 percent to about 1.0 percent by weight based on the organic phase.

5. The process of claim 3 wherein said dispersion includes a catalyst capable of increasing the rate of reaction of said organic polyisocyanate to form said polyurea.

6. The process of claim 5 wherein said catalyst is selected from the group consisting of a basic organic tertiary amine catalyst and an alkyl tin acetate catalyst.

7. The process of claim 1 wherein said dispersion includes a catalyst capable of increasing the rate of reaction of said organic polyisocyanate to form said polyurea.

8. The process of claim 7 wherein said catalyst is selected from the group consisting of a basic organic tertiary amine catalyst and an alkyl tin acetate catalyst.

9. The process of claim 1 wherein said water-immiscible phase contains a catalyst selected from the group consisting of (a) a basic organic tertiary amine catalyst in the amount of about 0.01 percent to about 10.0 percent by weight based on the organic phase and (b) an alkyl tin acetate catalyst in the amount of about 0.001 percent to about 1.0 percent by weight based on the organic phase.

10. Capsules capable of controlled release of encapsulated organic material comprising a thiocarbamate herbicide enclosed in a polyurea capsule produced by the process of claim 9.

11. Capsules capable of controlled release of encapsulated organic material comprising an organophosphorus insecticide enclosed in a polyurea capsule produced by the process of claim 9.

12. Capsules capable of controlled release of encapsulated organic material comprising an insect hormone mimic enclosed in a polyurea capsule produced by the process of claim 9.

13. The process of claim 1 wherein said organic polyisocyanate is aromatic diisocyanate.

14. The process of claim 13 wherein said aromatic diisocyanate comprises from about 2.0 percent to about 75.0 percent by weight of said water-immiscible phase.

15. The process of claim 13 wherein said aromatic diisocyanate is 80 percent 2,4- and 20 percent 2,6-isomer of tolylene diisocyanate.

16. The process of claim 1 wherein said water-immiscible material is water-immiscible organic material.

17. The process of claim 16 wherein said water-immiscible organic material is a thiocarbamate herbicide.

18. The process of claim 16 wherein said water-immiscible organic material comprises at least two water-immiscible organic materials.

19. The process of claim 18 wherein said water-immiscible organic material comprises a thiocarbamate herbicide and an antidote therefor.

20. The process of claim 16 wherein said water-immiscible organic material is an organophosphorous insecticide.

21. The process of claim 16 wherein said water-immiscible organic material is an insect hormone mimic.

22. The process of claim 1 wherein said dispersion is heated and maintained in a temperature range of about 40° C. to about 60° C.

23. Capsules capable of controlled release of encapsulated organic material comprising a thiocarbamate herbicide enclosed in a polyurea microcapsule produced by the process of claim 1.

24. Capsules of claim 23 in which said thiocarbamate herbicide is S-ethyl diisobutylthiocarbamate.

25. Capsules of claim 23 in which said thiocarbamate herbicide is S-ethyl dipropylthiocarbamate.

26. Capsules of claim 23 in which said thiocarbamate herbicide is S-ethyl hexahydro-1-H-azepine-1-carbothioate.

27. Capsules of claim 23 in which said thiocarbamate herbicide is S-propyl dipropylthiocarbamate.

28. Capsules of claim 23 in which said thiocarbamate herbicide is S-ethyl ethylcyclohexylthiocarbamate.

29. Capsules of claim 23 in which said thiocarbamate herbicide is S-propyl butylethylthiocarbamate.

30. Capsules of claim 23 in which said thiocarbamate herbicide is S-propyl hexahydro-1-H-azepine-1-carbothioate.

31. Capsules capable of controlled release of encapsulated organic material comprising an organophosphorus insecticide enclosed in a polyurea capsule produced by the process of claim 1.

32. Capsules of claim 1 in which said organophosphorus insecticide is O-ethyl S-phenyl ethylphosphonodithioate.

33. Capsules of claim 31 in which said organophosphorus insecticide is S[(p-chlorophenylthio)methyl] O,O-dimethyl phosphorodithioate.

34. Capsules of claim 31 in which said organophosphorus insecticide is S[(p-chlorophenylthio)methyl] O,O-diethyl phosphorodithioate.

35. Capsules of claim 31 in which said organophosphorus insecticide is O,O-dimethyl O-p-nitrophenyl phosphorothioate.

36. Capsules of claim 31 in which said organophosphorus insecticide is O,O-diethyl O-p-nitrophenyl phosphorothioate.

37. Capsules capable of controlled release of encapsulated organic material comprising an insect hormone mimic enclosed in a polyurea capsule produced by the process of claim 1.

38. Capsules of claim 37 in which said insect hormone mimic is 1-(4'-ethyl)phenoxy-3,7-dimethyl-6,7-epoxy-trans-2-octene.

39. A process of encapsulating water-immiscible material within discrete capsules of polyurea without addition of a second reactant, whereby hydrolysis of an isocyanate monomer to form an amine takes place which in turn reacts with another isocyanate monomer to form polyurea, which comprises the steps:
(a) providing in an aqueous phase at room temperature a solution comprising water, a surfactant and a protective colloid;
(b) adding to said aqueous phase a water-immiscible phase comprising the water-immiscible material to be encapsulated and an organic polyisocyanate;
(c) dispersing at room temperature said water-immiscible phase in said aqueous phase;
(d) heating and maintaining the dispersed water-immiscible phase and aqueous phase in a temperature range of about 40° C. to about 90° C.; whereupon said water-immiscible material is encapsulated within discrete polyurea capsular enclosures directly usable without further separation or purification.

40. The process of claim 39 wherein the dispersed water-immiscible phase comprises droplets having a particle size of between about 0.5 microns to about 4000 microns.

41. The process of claim 40 wherein said dispersion is maintained by mild agitation.

42. The process of claim 39 in which said water-immiscible material is water-immiscible organic material.

43. The process of claim 42 for encapsulating water-immiscible organic material wherein the water-immiscible phase added to the aqueous phase contains organic polyisocyanate within the range of about 2.0 percent to about 75.0 percent by weight.

44. The process of claim 43 for encapsulating water-immiscible organic material wherein said organic polyisocyanate is aromatic polyisocyanate.

45. The process of claim 44 for encapsulating water-immiscible organic material wherein said aromatic polyisocyanate is polymethylene polyphenylisocyanate.

46. The process of claim 43 for encapsulating water-immiscible organic material wherein said organic polyisocyanate is an aromatic diisocyanate.

47. The process of claim 46 for encapsulating water-immiscible organic material wherein said aromatic diisocyanate is 80 percent 2,4- and 20 percent 2,6-isomer of tolylene diisocyanate.

48. The process of claim 42 for encapsulating water-immiscible organic material wherein the water-immiscible phase added to the aqueous phase contains a combination of organic polyisocyanates, the total amount of which is within the range of about 2.0 percent to about 75 percent by weight.

49. The process of claim 48 wherein said combination of organic polyisocyanates consists of polymethylene polyphenylisocyanate and 80 percent 2,4- and 20 percent 2,6-isomers of tolylene diisocyanate.

50. The process of claim 39 further comprising the step of adjusting the pH of said aqueous phase to a value between 0 and 14.

51. The process of claim 42 wherein said water-immiscible organic material is a thiocarbamate herbicide; whereupon said thiocarbamate herbicide is encapsulated within a polyurea capsular enclosure.

52. The process of claim 51 for encapsulating water-immiscible organic material within a polyurea capsule wherein said thiocarbamate herbicide is S-ethyl diisobutylthiocarbamate.

53. The process of claim 51 for encapsulating a water-immiscible organic material within a polyurea capsule wherein said thiocarbamate herbicide is S-ethyl dipropylthiocarbamate.

54. The process of claim 51 for encapsulating a water-immiscible organic material within a polyurea capsule wherein said thiocarbamate herbicide is S-ethyl hexahydro-1-H-azepine-1-carbothioate.

55. The process of claim 51 for encapsulating a water-immiscible organic material within a polyurea capsule wherein said thiocarbamate herbicide is S-propyl dipropyl-thiocarbamate.

56. The process of claim 51 for encapsulating a water-immiscible organic material within a polyurea capsule wherein said thiocarbamate herbicide is S-ethyl ethylcyclohexylthiocarbamate.

57. The process of claim 51 for encapsulating a water-immiscible organic material within a polyurea capsule wherein said thiocarbamate herbicide is S-propyl butylethylthiocarbamate.

58. The process of claim 51 for encapsulating a water-immiscible organic material within a polyurea capsule wherein said thiocarbamate herbicide is S-propyl hexahydro-1-H-azepine-1-carbothioate.

59. The process of claim 42 wherein said water-immiscible organic material is an organophosphorus insecticide, whereupon said organophosphorus insecticide is encapsulated within a polyurea capsular enclosure.

60. The process of claim 59 for encapsulating a water-immiscible organic material within a polyurea capsule wherein said organophosphorus insecticide is O-ethyl S-phenyl ethylphosphonodithioate.

61. The process of claim 59 for encapsulating a water-immiscible organic material within a polyurea capsule wherein said organophosphorus insecticide is O,O-dimethyl O-p-nitrophenyl phosphorothioate.

62. The process of claim 59 for encapsulating a water-immiscible organic material within a polyurea capsule wherein said organophosphorus insecticide is O,O-diethyl O-p-nitrophenyl phosphorothioate.

63. The process of claim 59 for encapsulating a water-immiscible organic material within a polyurea capsule wherein said organophosphorus insecticide is S-[(p-chlorophenylthio)methyl]O,O-dimethyl phosphorodithioate.

64. The process of claim 59 for encapsulating a water-immiscible organic material within a polyurea capsule wherein said organophosphorus insecticide is S-[(p-chlorophenylthio)methyl] O,O-diethyl phosphorodiothioate.

65. The process of claim 42 wherein said water-immiscible organic material is an insect hormone mimic, whereupon said insect hormone mimic is encapsulated within a polyurea capsular enclosure.

66. The process of claim 65 for encapsulating a water-immiscible organic material within a polyurea capsule wherein said insect hormone mimic is 1-(4'-ethyl)-phenoxy-3,7-dimethyl-6,7-epoxy-trans-2-octene.

67. The process of claim 42 wherein said water-immiscible organic material comprises at least two water-immiscible materials in the organic phase; whereupon said water-immiscible materials are encapsulated within a polyurea capsular enclosure.

68. The process of claim 67 wherein said water-immiscible materials are a thiocarbamate herbicide and an antidote therefor.

69. The process of claim 68 in which said thiocarbamate herbicide is S-ethyl dipropylthiocarbamate and said antidote is N,N-diallyldichloroacetamide.

70. The process of claim 39 wherein said dispersed water-immiscible phase and aqueous phase is heated and maintained in a temperature range of about 40° C. to about 60° C.

71. The process of claim 39 wherein said water-immiscible phase contains a catalyst capable of increasing the rate of reaction of said organic polyisocyanate to form said polyurea.

72. The process of claim 71 wherein said catalyst is selected from the group consisting of a basic organic tertiary amine catalyst and an alkyl tin acetate catalyst.

73. Capsules capable of controlled release of encapsulated organic material comprising a thiocarbamate herbicide enclosed in a polyurea capsule produced by the process of claim 39.

74. Capsules capable of controlled release of encapsulated organic material comprising an organophosphorus insecticide enclosed in a polyurea capsule produced by the process of claim 39.

75. Capsules capable of controlled release of encapsulated organic material comprising an insect hormone mimic enclosed in a polyurea capsule produced by the process of claim 39.

76. A process of encapsulating water-immiscible material within discrete capsules of polyurea without addition of a second reactant, whereby hydrolysis of an isocyanate monomer to form an amine takes place which in turn reacts with another isocyanate monomer to form polyurea, which comprises the steps:
(a) providing in an aqueous phase at room temperature a solution comprising water and a surfactant;
(b) adding to said aqueous phase a water-immiscible phase comprising a water-immiscible material to be encapsulated and an organic polyisocyanate;
(c) dispersing at room temperature said water-immiscible phase in said aqueous phase to form a dispersion of droplets of the water-immiscible phase in said aqueous phase;
(d) adding to said dispersion a protective colloid;
(e) heating and maintaining said dispersion in a temperature range of about 40° C. to about 90° C. with mild agitation; whereupon said water-immiscible material is encapsulated within discrete polyurea capsular enclosures directly usable without further separation or purification.

77. The process of claim 76 wherein the temperature range is about 40° C. to about 60° C.

78. The process of claim 76 wherein the dispersion contains a catalyst capable of increasing the rate of reaction of said organic polyisocyanate to form said polyurea.

79. A process of encapsulating water-immiscible material within discrete capsules of polyurea without addition of a second reactant, whereby hydrolysis of an isocyanate monomer to form an amine takes place which in turn reacts with another isocyanate monomer to form polyurea, which comprises the steps:
(a) providing, at room temperature, a dispersion comprising (i) a water-immiscible phase comprising the water-immiscible material to be encapsulated and an organic polyisocyanate in (ii) an aqueous phase comprising a solution of water, a surfactant and a protective colloid, which dispersion contains a catalyst capable of increasing the rate of reaction of said organic polyisocyanate to form said polyurea; and
(b) maintaining said dispersion at room temperature whereupon said water-immiscible material is encapsulated within discrete polyurea capsular enclosures directly usable without further separation or purification.

80. The process of claim 79 wherein the dispersed water-immiscible phase comprises droplets having a particle size of between about 0.5 microns to about 4000 microns.

81. The process of claim 79 wherein said dispersion is maintained by mild agitation.

82. The process of claim 79 wherein said catalyst is selected from the group consisting of a basic organic tertiary amine catalyst and an alkyl tin acetate catalyst.

83. The process of claim 79 wherein said catalyst is selected from the group consisting of (a) a basic organic tertiary amine catalyst in the amount of about 0.01 percent to about 10.0 percent by weight based on the organic phase and (b) an alkyl tin acetate catalyst in the amount of about 0.001 percent to about 1.0 percent by weight based on the organic phase.

84. The process of claim 79 wherein said catalyst is a basic organic tertiary amine catalyst in the amount of about 0.01 percent to about 10.0 percent by weight based on the organic phase.

85. The process of claim 84 wherein said catalyst is selected from the group consisting of triethylene diamine, N,N,N',N'-tetramethyl-1,3-butane diamine, triethylamine and tri-n-butyl amine.

86. The process of claim 79 wherein said catalyst is an alkyl tin acetate catalyst in the amount of about 0.001 percent to about 1.0 percent by weight based on the organic phase.

87. The process of claim 86 wherein said catalyst is selected from the group consisting of tri-butyl tin acetate and di-n-butyl tin diacetate.

88. The process of claim 79 wherein the pH of said aqueous phase is adjusted to a value between 0 and 14.

89. The process of claim 79 wherein said catalyst is added to said dispersion after said dispersion is formed.

90. The process of claim 79 wherein said organic polyisocyanate is an aromatic diisocyanate.

91. The process of claim 90 wherein said aromatic diisocyanate comprises from about 2.0 percent to about 75.0 percent by weight of said water-immiscible phase.

92. The process of claim 90 wherein said aromatic diisocyanate is 80 percent 2,4- and 20 percent 2,6-isomer of tolylene diisocyanate.

93. The process of claim 79 wherein said water-immiscible material is water-immiscible organic material.

94. The process of claim 93 wherein said water-immiscible organic material is a thiocarbamate herbicide.

95. The process of claim 93 wherein said water-immiscible organic material is an organophosphorous insecticide.

96. The process of claim 93 wherein said water-immiscible organic material is an insect hormone mimic.

97. The process of claim 93 wherein said water-immiscible organic material comprises at least two water-immiscible organic materials.

98. The process of claim 97 wherein said water-immiscible organic material comprises a thiocarbamate herbicide and an antidote therefor.

99. A process for encapsulating water-immiscible material within discrete capsules of polyurea without addition of a second reactant, whereby hydrolysis of an isocyanate monomer to form an amine takes place which in turn reacts with another isocyanate monomer to form polyurea, which comprises the steps:
  (a) providing, at room temperature, in an aqueous phase a solution comprising water and a surfactant;
  (b) adding to said aqueous phase, at room temperature, a water-immiscible phase comprising organic polyisocyanate, a water-immiscible material to be encapsulated, and a catalyst capable of increasing the rate of reaction of said organic polyisocyanate to form polyurea;
  (c) dispersing said water-immiscible phase in said aqueous phase to establish droplets of the water-immiscible phase in the aqueous phase;
  (d) maintaining the dispersion at room temperature; and
  (e) adding to the dispersion a protective colloid; whereupon said water-immiscible material is encapsulated within discrete polyurea capsular enclosures directly usable without further separation or purification.

100. The process of claim 99 wherein said catalyst is selected from a group consisting of (a) a basic organic tertiary amine catalyst in the amount of about 0.01 percent to about 10.0 percent by weight based on the organic phase and (b) an alkyl tin acetate catalyst in the amount of about 0.001 percent to about 1.0 percent by weight based on the organic phase.

101. A process according to claim 99 which further comprises the step of adjusting the pH of said aqueous phase to a value between 0 and 14.

102. The process of claim 99 wherein the dispersed water-immiscible phase comprises droplets having a particle size of between about 0.5 microns to about 4000 microns.

103. The process of claim 102 wherein said dispersion is maintained by mild agitation.

104. The process of claim 104 wherein said catalyst is selected from the group consisting of a basic organic tertiary amine catalyst and an alkyl tin acetate catalyst.

105. The process of claim 104 wherein said water immiscible phase contains a catalyst selected from the group consisting of (a) a basic organic tertiary amine catalyst in the amount of about 0.01 percent to about 10.0 percent by weight based on the organic phase and (b) an alkyl tin acetate catalyst in the amount of about 0.001 percent to about 1.0 percent by weight based on the organic phase.

106. The process of claim 99 in which said water-immiscible material is water-immiscible organic material, whereupon said water-immiscible organic material is encapsulated within a polyurea capsular enclosure.

* * * * *

UNITED STATES PATENT AND TRADEMARK OFFICE
CERTIFICATE OF CORRECTION

PATENT NO. : 4,285,720
DATED : August 25, 1981
INVENTOR(S) : Herbert B. Scher

It is certified that error appears in the above—identified patent and that said Letters Patent is hereby corrected as shown below:

In Column 6, at line 32, the figure "0.1" should read --- 0.01 ---.

In Column 16, Claim 32 should read as being dependent upon Claim 31.

In Column 22, Claim 104 should read as being dependent upon Claim 103.

In Column 22, Claim 105 should read as being dependent upon Claim 103.

Signed and Sealed this

Twentieth Day of July 1982

[SEAL]

Attest:

GERALD J. MOSSINGHOFF

Attesting Officer    Commissioner of Patents and Trademarks